United States Patent
Ruffolo, Jr.

(10) Patent No.: US 7,528,145 B2
(45) Date of Patent: May 5, 2009

(54) USE OF AN MTOR INHIBITOR IN TREATMENT OF UTERINE LEIOMYOMA

(75) Inventor: Robert R. Ruffolo, Jr., Spring City, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/255,267

(22) Filed: Oct. 21, 2005

(65) Prior Publication Data

US 2006/0094745 A1 May 4, 2006

Related U.S. Application Data

(60) Provisional application No. 60/622,917, filed on Oct. 28, 2004.

(51) Int. Cl.
*A61K 31/4745* (2006.01)
(52) U.S. Cl. .................................................. 514/291
(58) Field of Classification Search ................ 514/291
See application file for complete search history.

(56) References Cited

U.S. PATENT DOCUMENTS

| | | | |
|---|---|---|---|
| 4,316,885 A | 2/1982 | Rakhit | |
| 4,650,803 A | 3/1987 | Stella et al. | |
| 5,023,263 A | 6/1991 | Von Burg | |
| 5,023,264 A | 6/1991 | Caufield et al. | |
| 5,100,883 A | 3/1992 | Schiehser | |
| 5,118,677 A | 6/1992 | Caufield | |
| 5,118,678 A | 6/1992 | Kao et al. | |
| 5,120,842 A | 6/1992 | Failli et al. | |
| 5,162,333 A | 11/1992 | Failli et al. | |
| 5,177,203 A | 1/1993 | Failli et al. | |
| 5,221,670 A | 6/1993 | Caufield | |
| 5,233,036 A | 8/1993 | Hughes | |
| 5,256,790 A | 10/1993 | Nelson | |
| 5,260,300 A | 11/1993 | Hu et al. | |
| 5,262,423 A | 11/1993 | Kao et al. | |
| 5,302,584 A | 4/1994 | Kao et al. | |
| 5,362,718 A | 11/1994 | Skotnicki et al. | |
| 5,373,014 A | 12/1994 | Failli et al. | |
| 5,378,836 A | 1/1995 | Kao et al. | |
| 5,385,908 A | 1/1995 | Nelson et al. | |
| 5,385,909 A | 1/1995 | Nelson et al. | |
| 5,385,910 A | 1/1995 | Ocain et al. | |
| 5,389,639 A | 2/1995 | Failli et al. | |
| 5,391,730 A | 2/1995 | Skotnicki et al. | |
| 5,411,967 A | 5/1995 | Kao et al. | |
| 5,434,260 A | 7/1995 | Skotnicki et al. | |
| 5,463,048 A | 10/1995 | Skotnicki et al. | |
| 5,480,988 A | 1/1996 | Failli et al. | |
| 5,480,989 A | 1/1996 | Kao et al. | |
| 5,489,680 A | 2/1996 | Failli et al. | |
| 5,491,231 A | 2/1996 | Nelson et al. | |
| 5,504,091 A | 4/1996 | Molnar-Kimber et al. | |
| 5,536,729 A | 7/1996 | Waranis | |
| 5,563,145 A | 10/1996 | Failli et al. | |
| 5,665,591 A * | 9/1997 | Sonenshein et al. | 435/375 |
| 5,665,772 A | 9/1997 | Cottens et al. | |
| 5,780,462 A | 7/1998 | Lee et al. | |
| 5,989,591 A | 11/1999 | Nagi | |
| 6,218,594 B1 | 4/2001 | Tsibris | |
| 6,277,983 B1 * | 8/2001 | Shaw et al. | 540/456 |
| 6,329,386 B1 * | 12/2001 | Mollison | 514/291 |
| 6,511,986 B2 * | 1/2003 | Zhang et al. | 514/280 |
| 6,617,333 B2 * | 9/2003 | Rabindran et al. | 514/291 |
| 2003/0144204 A1 | 7/2003 | Spencer | |
| 2004/0077677 A1 | 4/2004 | Ashraf et al. | |
| 2004/0106637 A1 | 6/2004 | Guan | |
| 2004/0167152 A1 | 8/2004 | Rubino | |
| 2004/0176339 A1 * | 9/2004 | Sherman et al. | 514/171 |
| 2005/0033046 A1 | 2/2005 | Chew et al. | |

FOREIGN PATENT DOCUMENTS

| | | |
|---|---|---|
| GB | WO 2004/082681 A1 * | 9/2004 |
| WO | WO 95/28406 A1 | 10/1995 |
| WO | WO 98/02441 | 1/1998 |
| WO | WO 99/01118 A2 | 1/1999 |
| WO | WO 99/01118 A3 | 1/1999 |
| WO | WO99/15530 | 4/1999 |
| WO | WO 01/14387 | 3/2001 |
| WO | WO 2004/011000 A1 | 2/2004 |
| WO | WO 2004/026280 A3 | 4/2004 |
| WO | WO2005016935 A3 | 2/2005 |

OTHER PUBLICATIONS

Goncharova et al. J. Bio. Chem. vol. 277 (34) 30958-30967.*
Hidalgo et al. Proc Am Soc Clin Oncol 19: 2000 (abstr 726) 2 pages.*
Lee et al. The J. Clin. Endoc. & Metabolism vol. 86 (2), 913-920, 2001.*
Houston et al, Inhibition of Proliferation and Estrogen Receptor Signaling by Peroxisome Proliferator—Activated Receptor γ Ligands in Uterine Leiomyoma, Cancer Research, 63:1221-1227. (2003).

(Continued)

*Primary Examiner*—Michael G Hartley
*Assistant Examiner*—Shirley V Gembeh
(74) *Attorney, Agent, or Firm*—Howson & Howson LLP; David A. Rubin

(57) ABSTRACT

The invention provides for the use of an mTOR inhibitor in the treatment or inhibition of fibroids.

3 Claims, No Drawings

OTHER PUBLICATIONS

Tsibris et al, Human Uterine Leiomyomata Express Higher Levels of Peroxisome Proliferator-Activated Receptor γ, Retinoid χ Receptor α, and all-trans Retinoic Acid than Myometrium, Cancer Res. 59:5737, (1999).

Walker et al, Preclinical Evidence for Therapeutic Efficacy of Selective Estrogen Receptor Modulators for Uterine Leiomyoma, J. Soc. Gynecol Investing., vol. 7, No. 4, (Jul./Aug. 2000).

Walker et al, Uterine Leiomyoma in the Eker Rat: A Unique model for Important Diseases of Women, Genes, Chromosomes & Cancer, 38:349-356, (Jul. 2003).

Tsibris et al, Effect of Troglitazone, an Inducer of the Peroxisome Proliferator-Activated Receptor γ (PPARγ), on Uterine Leiomyoma Development in the Guinea Pig Model, J. Soc. Gyynecol. Invest. 5(suppl. 1):180(abstract), (Jan./Feb. 1998).

* cited by examiner

USE OF AN MTOR INHIBITOR IN TREATMENT OF UTERINE LEIOMYOMA

CROSS-REFERENCE TO RELATED APPLICATIONS

This application claims the benefit under 35 USC 119(e) of prior U.S. Provisional Patent Application No. 60/622,917, filed Oct. 28, 2004.

BACKGROUND OF THE INVENTION

This invention relates to the use of an mTOR inhibitor in the treatment or inhibition of uterine leiomyoma (fibroids) in a mammal.

mTOR, also known as FKBP12-rapamycin associated protein (FRAP), is a key enzyme in a variety of signal transduction pathways, including cytokine-stimulated cell proliferation, translation of mRNAs for several key proteins that regulate the G1 phase of the cell cycle, and interleukin-2 (IL-2) induced transcription. Inhibition of mTOR leads to the inhibition of the progression of the cell cycle from G1 to S. Rapamycin (commercially available as Sirolimus™), a macrocycline triene antibiotic produced by *Streptomyces hygroscopicus*, has been identified as a key mTOR inhibitor.

Rapamycin 42-ester with 3-hydroxy-2-(hydroxymethyl)-2-methylpropionic acid (CCI-779) is an ester of rapamycin. The preparation and use of hydroxyesters of rapamycin, including CCI-779, are described in U.S. Pat. Nos. 5,362,718 and 6,277,983. Still another regioselective method for synthesis of CCI-779 is described in U.S. patent application Ser. No. 10/903,062, filed Jul. 30, 2004 (published Feb. 10, 2005 as U.S. Patent Publication No. US 2005-0033046 A1), and its counterpart, International Patent Application No. PCT/US2004/22860 (published Feb. 24, 2005 as International Patent Publication No. WO 2005/016935 A3). CCI-779 has been described as having an in vitro and in vivo activity against a number of tumor cell types. CCI-779 binds to and forms a complex with the cytoplasmic protein FKBP, which inhibits mTOR. It is hypothesized that CCI-779 delays the tire to progression of tumors or time to tumor recurrence. This mechanism of action is more typical of cytostatic rather than cytotoxic agents and is similar to that of sirolimus.

Uterine leiomyoma (fibroids) are benign tumors arising from the myometrium (smooth muscle layer) of the uterus. Leiomyoma are the most common solid pelvic tumor of women and are 2-5 times more likely to occur in black women than white women. Fibroids occur in as many as 75% of reproductive age women, with 25% of these women symptomatic to the point of seeking treatment. Women with symptomatic fibroids suffer from menorrhagia, pelvic pain and pressure, and are more subject to reproductive dysfunction such as infertility or multiple miscarriages.

The primary treatment for patients with fibroids is surgery—either myomectomy for removal of tumor and preservation of childbearing potential, or hysterectomy. Fibroids are the most common indication for hysterectomy and account for approximately 200,000 procedures performed annually in the United States.

Thus, there is a need in the art for more effective methods of treating and inhibiting fibroids.

SUMMARY OF THE INVENTION

The invention provides for the use of an mTOR inhibitor in treating or inhibiting, or in the preparation of a medicament useful in treating or inhibiting, uterine leiomyoma (fibroids) in a female mammalian subject. In another aspect, the invention provides for the use of a rapamycin in treating or inhibiting, or in the preparation of a medicament useful in treating or inhibiting, uterine leiomyoma in a female mammalian subject. In one embodiment, the invention provides the use of rapamycin or CCI-779 in treating or inhibiting, or in the preparation of a medicament useful in treating or inhibiting, uterine leiomyoma in a female mammalian subject.

In other aspects, the invention provides for pharmaceutical compositions comprising an mTOR inhibitor, and in certain embodiments, a rapamycin, rapamycin, or CCI-779, in unit dosage form in association with a pharmaceutically acceptable carrier, which are useful in treating or inhibiting uterine leiomyoma in a female mammalian subject.

In yet another embodiment, the invention provides for pharmaceutical packs containing a course of treatment of uterine leiomyoma for one individual mammal, each pack comprising a container having one unit, one to four units, or more units of an mTOR inhibitor, and in certain embodiments, a rapamycin, rapamycin or CCI-779 in unit dosage form.

Other aspects and advantages of the invention will be apparent from the following detailed description of the invention.

DETAILED DESCRIPTION OF THE INVENTION

The present invention provides methods of using an effective amount of an mTOR inhibitor in the treatment or inhibition of, or in the preparation of a medicament useful in treating or inhibiting, uterine leiomyoma (fibroids). In one embodiment, an effective amount of rapamycin is useful in methods of treating or inhibiting fibroids. In another embodiment, an effective amount of CCI-779 (rapamycin 42-ester with 3-hydroxy-2-(hydroxymethyl)-2-methylpropionic acid) is useful in methods of treating or inhibiting fibroids. Other compounds useful in the methods of the invention in treating or inhibiting fibroids include effective amounts of a rapamycin, such as esters (including 42-esters), ethers (including 42-ethers), oximes, hydrazones, and hydroxylamines of rapamycin. In another embodiment, the invention provides for methods of treating or inhibiting fibroids using an effective amount of 42-O-(2-hydroxy)ethyl rapamycin (Certican™ (everolimus)).

In another embodiment, FK-506 is useful in methods of treating or inhibiting fibroids. In another embodiment, AP23573 is useful in methods of treating or inhibiting fibroids.

As used herein, the term fibroid or fibroids shall have the same meaning as uterine leiomyoma, as described above.

As used herein, the term mTOR inhibitor means a compound or ligand, or a pharmaceutically acceptable salt thereof, that inhibits cell replication by blocking the progression of the cell cycle from G1 to S. The term includes the neutral tricyclic compound rapamycin (sirolimus) and other rapamycin compounds, including, e.g., rapamycin derivatives, rapamycin analogues, other macrolide compounds that inhibit mTOR activity, and all compounds included within the definition below of the term "a rapamycin".

These include compounds with a structural similarity to "a rapamycin", e.g., compounds with a similar macrocyclic structure that have been modified to enhance therapeutic benefit. The term also includes, e.g., rapamycin, 32-deoxorapamycin, 16-pent-2-ynyloxy-32-deoxorapamycin, 16-pent-2-ylyloxy-32(S) -dihydro-rapamycin, 16-pent-2-ylyloxy-32(S)-dihydr-o-40-O-(2-hydroxyethyl)-rapamycin, 40-O-(2-hydroxyethyl)-rapamycin, rapamycin 42-ester with 3-hydroxy-2-(hydroxymethyl)-2-methylpropionic acid (CCI-779), 40-[3-hydroxy-2-(hydroxymethyl)-2-meth-yl-propanoate]-rapamycin, or a pharmaceutically acceptable salt thereof, as disclosed in U.S. Pat. No. 5,362,718, ABT578, or 40-(tetrazolyl)-rapamycin, 40-epi-(tetrazolyl)-rapamycin, e.g., as disclosed in International Patent Publication No. WO 99/15530, or rapamycin analogs as disclosed in International Patent Publication No. WO 98/02441 and WO 01/14387, e.g., AP23573.

FK-506 can also be used in the method of the invention.

As used herein, the term a rapamycin defines a class of immunosuppressive compounds that contain the basic rapamycin nucleus as shown below.

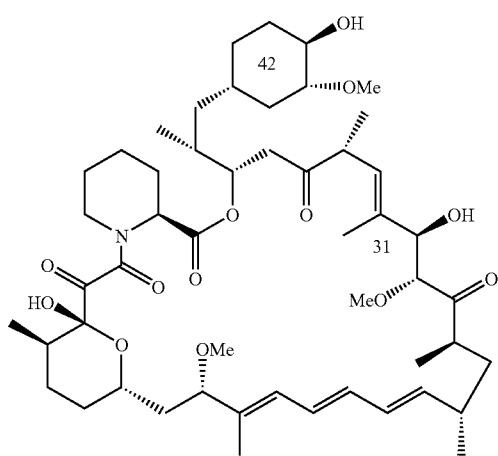

The rapamycins of this invention include compounds that are chemically or biologically modified as derivatives of the rapamycin nucleus, while still retaining immunosuppressive properties. Accordingly, the term a rapamycin includes rapamycin, and esters, ethers, carbamates, oximes, hydrazones, and hydroxylamines of rapamycin, as well as rapamycins in which functional groups on the rapamycin nucleus have been modified, for example through reduction or oxidation. Also included in the term a rapamycin are pharmaceutically acceptable salts of rapamycins.

The term a rapamycin also includes 42- and/or 31-esters and ethers of rapamycin as described in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl esters (U.S. Pat. No. 5,120,842); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers is disclosed in the patents listed above.

Further included within the definition of the term a rapamycin are 27-esters and ethers of rapamycin, which are disclosed in U.S. Pat. No. 5,256,790, which is hereby incorporated by reference. Also described are C-27 ketone rapamycins which are reduced to the corresponding alcohol, which is in turn converted to the corresponding ester or ether. The preparation of these esters and ethers is disclosed in the patent listed above. Also included are oximes, hydrazones, and hydroxylamines of rapamycin are disclosed in U.S. Pat. Nos. 5,373,014, 5,378,836, 5,023,264, and 5,563,145, which are hereby incorporated by reference. The preparation of these oximes, hydrazones, and hydroxylamines is disclosed in the above-listed patents. The preparation of 42-oxorapamycin is disclosed in U.S. Pat. No. 5,023,263, which is hereby incorporated by reference.

As used herein, the term a CCI-779 means rapamycin 42-ester with 3-hydroxy-2-(hydroxymethyl)-2-methylpropionic acid, and encompasses prodrugs, derivatives, pharmaceutically acceptable salts, or analogs thereof.

As used herein, the term treatment means treating a mammal having fibroids (uterine leiomyoma) by providing said mammal with an effective amount of a compound or composition for the purpose of inhibiting growth of the fibroid, eradication of the fibroid, or palliation of the fibroid.

As used herein, the term inhibition means delaying or preventing the onset or progression of fibroids in a mammal having or susceptible to developing such disease by providing said mammal with an effective amount of a compound or composition of the invention.

As used herein, the term providing means either directly administering a compound or composition of the invention or administering a prodrug, derivative, pharmaceutical salt, or analog of an mTOR inhibitor, which will result in a desired amount of the compound or composition in the body.

All terms used herein, whether used in the singular or plural form, shall include both the singular and plural form unless otherwise indicated.

As used herein, the terms include, includes, and including indicates that the subject is open to other items, i.e., an open class.

As used herein, the terms comprise, comprises, and comprising indicates that the subject is open to other items, i.e., an open class.

As used herein, the terms contain, contains, and containing indicates that the subject is open to other items, i.e., an open class.

As used herein, the terms consists of and consisting of indicates that the subject is closed to other items, i.e., a closed class.

All other terms used herein shall be defined as expressly or impliedly defined within this specification, and then, if necessary, in accordance with their interpretation by one of ordinary skill in the relevant art.

Compositions/Formulations

Compositions useful in the present invention comprise an active compound (e.g., an mTOR inhibitor) as described herein. In one embodiment, the compound is CCI-779 (rapamycin 42-ester with 3-hydroxy-2-(hydroxymethyl)-2-methylpropionic acid)(U.S. Pat. No. 5,362,718). The preparation of CCI-779 is disclosed in U.S. Pat. No. 5,362,718, which is hereby incorporated by reference. A regioselective preparation of CCI-779 is described in U.S. Pat. No. 6,277,983. Still another regiospecific method for synthesis of CCI-779 is described in U.S. patent application Ser. No. 10/903,062, filed Jul. 30, 2004, and its counterpart, International Patent Application PCT/US2004/22860, filed Jul. 15, 2004. Rapamycin is commercially available as Sirolimus™.

In another embodiment, the compound is AP23573. In another embodiment, the compound is Certican™ (everolimus). Other compounds useful in the methods, compositions, and pharmaceutical packs of the invention include a rapamycin, such as rapamycin, esters (including 42-esters), ethers (including 42-ethers), oximes, hydrazones, and hydroxylamines of rapamycin. In another embodiment, the rapamycin is 42-O-(2-hydroxy)ethyl rapamycin (everolimus, Novartis, U.S. Pat. No. 5,665,772, hereby incorporated by reference). In other embodiments, compositions of the present invention contain other compounds useful in the invention as described herein.

In yet another embodiment, the compound is FK-506.

Administration of the compositions may be oral, intravenous, respiratory (e.g., nasal or intrabronchial), parenteral, intraperitoneal, transdermal (including all administration across the surface of the body and the inner linings of bodily passages including epithelial and mucosal tissues), and vaginal (including intrauterine administration).

It is projected that the oral dosage of a compound useful in the invention will be 10 mg/week to 250 mg/week, about 20 mg/week to about 150 mg/week, about 25 mg/week to about 100 mg/week, or about 30 mg/week to about 75 mg/week. For rapamycin, the projected oral dosage will be between 0.1 mg/day to 25 mg/day. Intravenous dosages are generally predicted to be five to tenfold less than oral dosages. Precise dosages will be determined by the administering physician based on experience with the individual subject to be treated.

In one embodiment, the pharmaceutical composition is in unit dosage form, e.g., as tablets, capsules, or pre-filled vials or syringes. In such form, the composition is sub-divided in unit dose containing appropriate quantities of the active ingredient; the unit dosage forms can be packaged compositions, for example, packeted powders, vials, ampoules, pre-filled syringes or sachets containing liquids. The unit dosage form can be, for example, a capsule or tablet itself, or it can be the appropriate number of any such compositions in package form.

Oral formulations containing the compounds of this invention may comprise any conventionally used forms, including tablets, capsules, buccal forms, troches, lozenges and oral liquids, suspensions or solutions. Capsules may contain mixtures of the active compound(s) with inert fillers and/or diluents such as pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium laurel sulfate, microcrystalline cellulose, carboxymethylcellulose calcium, polyvinylpyrrolidone, gelatin, alginic acid, acacia gum, xantham gum, sodium citrate, complex silicates, calcium carbonate, glycine, dextrin, sucrose, sorbitol, dicalcium phosphate, calcium sulfate, lactose, kaolin, mannitol, sodium chloride, dry starches and powdered sugar. Surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize delay or time release formulations to alter the absorption of the active compound(s). The oral formulation may also comprise administering the active compound in water or a fruit juice, containing appropriate solubilizers or emulsifiers as needed. Preferred oral formulations for CCI-779 are disclosed in U.S. Published Patent Application No. US 2004-0077677 A1 (also U.S. patent application Ser. No. 10/663,506). Preferred solid oral formulations for rapamycin are disclosed in U.S. Pat. No. 5,989,591, and preferred oral liquid formulations for rapamycin are disclosed in U.S. Pat. No. 5,536,729.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils. In one embodiment, injectable formulations for CCI-779 are disclosed in U.S. Patent Publication No. US 2004-0167152 (also U.S. patent application Ser. No. 10/626,943), which is hereby incorporated by reference.

In one embodiment, the injectable formulation useful in the invention provides a compound in a cosolvent concentrate containing a parenterally acceptable solvent and an antioxidant as described above and a parenteral formulation containing a compound useful in the invention, a parenterally acceptable cosolvent, an antioxidant, a diluent solvent, and a surfactant. Any given formulation useful in this invention may contain multiple ingredients of each class of component. For example, a parenterally acceptable solvent can include a nonalcoholic solvent, an alcoholic solvent, or mixtures thereof.

Examples of suitable non-alcoholic solvents include, e.g., dimethylacetamide, dimethylsulfoxide or acetonitrile, or mixtures thereof. An alcoholic solvent may contain one or more alcohols as the alcoholic solvent component of the formulation. Examples of solvents useful in the formulations of the invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v ethanol in the mixture is preferred.

In another embodiment, the stability of a compound useful in the invention in parenterally acceptable alcoholic solvents is enhanced by addition of an antioxidant to the formulation. Acceptable antioxidants include, but are not limited to, citric acid, d,1-α-tocopherol, BHA, BHT, monothioglycerol, ascorbic acid, propyl gallate, and mixtures thereof. Generally, the parenteral formulations useful in this embodiment will contain an antioxidant component(s) in a concentration ranging from 0.001% to 1% w/v, or 0.01% to 0.5% w/v, of the cosolvent concentrate although lower or higher concentrations may be desired. In one embodiment, of the antioxidants, d,1-α-tocopherol is particularly desirable and is used at a concentration of 0.01 to 0.1% w/v with a preferred concentration of 0.075% w/v of the cosolvent concentrate.

In other embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations). Other chelating agents include such materials as are capable of binding metal ions in solution, such as ethylene diamine tetra acetic acid (EDTA), its salts, or amino acids such as glycine are capable of enhancing the stability of a compound useful in the invention. In some embodiments, components with chelating activity are included in the formulations of the invention as the sole antioxidant component. Typically, such metal-binding components, when acting as chelating agents are used in the lower end of the range of concentrations for the antioxidant components provided herein. Higher concentrations yield less stable solutions and thus, less desirable for products to be subject to long-term storage in liquid form. Additionally, such chelating agents may be used in combination with other antioxidants as part of the antioxidant component of the invention. For example, an acceptable formulation may contain both citric acid and d,1-α-tocopherol. Optimal concentrations for the selected antioxidant(s) can be readily determined by one of ordinary skill in the art, based upon the information provided herein.

In certain embodiments of the parenteral formulations useful in the invention, surfactants are used in the diluent solution to prevent precipitation of the components of the formulation. Parenterally acceptable surfactants may be readily selected by one of ordinary skill in the art and include: polysorbate 20, polysorbate 80, salts of bile acids (taurocholate, glycocholate, cholate, deoxycholate, etc.), which are optionally combined with lecithin. Alternatively, ethoxylated vegetable oils, such as a pegylated castor oil (e.g., such as PEG-35 castor oil which is sold, e.g., under the name Cremophor EL, BASF), vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60. Other components of the diluent may include water, ethanol, polyethylene glycol 300, polyethylene glycol 400, polyethylene glycol 600, polyethylene glycol 1000, or blends containing one or more of these polyethylene glycols, propylene glycol and other parenterally acceptable sugars, polyols and electrolytes. It is expected that the surfactant will comprise 2 to 100% w/v, 5 to 80% w/v, 10 to 75% w/v, 15 to 60% w/v, 5% w/v, or 10% w/v, of the diluent solution.

A parenteral formulation useful in the invention can be prepared as a single solution, or can be prepared as a cosolvent concentrate containing a compound useful in the invention, an alcoholic solvent, and an antioxidant, which is subsequently combined with a diluent that contains a diluent solvent and suitable surfactant. Prior to use, the cosolvent concentrate is mixed with a diluent comprising a diluent solvent, and a surfactant. In one embodiment, a compound useful in the invention is prepared as a cosolvent concentrate according to the invention, having concentrations of compound from 0.05 mg/mL, from 2.5 mg/mL, from 5 mg/mL, from 10 mg/mL, or from 25 mg/mL up to approximately 50 mg/mL. The concentrate can be mixed with the diluent up to approximately 25 mg/mL. For example, the concentration of a compound useful in the invention in the parenteral formulation may be from about 2.5 to 10 mg/mL. This invention also covers the use of formulations having lesser concentrations of a compound useful in the invention in the cosolvent concentrate, and formulations in which one part of the concentrate is mixed with greater than 1 part of the diluent, e.g., concentrate:diluent in a ratio of about 1:1.5, 1:2, 1:3, 1:4, 1:5, or 1:9 v/v, and so on, to parenteral formulations having compound concentrations down to the lowest levels of detection.

In another embodiment, the antioxidant may comprise from about 0.0005 to 0.5% w/v of the formulation. The surfactant may, for example, comprise from about 0.5% to about 10% w/v of the formulation. The alcoholic solvent may be, for example, from about 10% to about 90% w/v of the formulation.

In other embodiments, the parenteral formulations useful in this invention can be used to produce a dosage form that is suitable for administration by either direct injection or by addition to sterile infusion fluids for intravenous infusion.

Transdermal administration may be accomplished through the use of a transdermal patch containing the active compound and a carrier that is inert to the active compound, is non-toxic to the skin, and allows delivery of the agent for systemic absorption into the blood stream via the skin. Such administrations may be carried out using the compounds useful in the invention, or pharmaceutically acceptable salts thereof, in lotions, creams, foams, patches, suspensions, solutions, and suppositories (rectal and vaginal). The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient into the blood stream such as a semi-permeable membrane covering a reservoir containing the active compound into the blood stream such as a semi-permeable membrane covering a reservoir containing the active compound with or without a carrier, or a matrix containing the active compound. Other occlusive devices are known in the literature and would be readily available to one of skill in the art.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

In one embodiment, the compositions are delivered vaginally in the form of a conventional suppository, cream, gel, ring, or coated intrauterine device (IUD).

Pharmaceutical Packs/Kits

The invention includes a product or pharmaceutical pack containing a course of treatment of uterine leiomyoma for one individual mammal comprising one or more container(s) having one, one to four, or more unit(s) of an mTOR inhibitor (e.g., CCI-779) in unit dosage form In another embodiment, pharmaceutical packs contain a course of treatment of uterine leiomyoma for one individual mammal comprising a container having a unit of a rapamycin in unit dosage form. In other embodiments, the rapamycin is rapamycin, an ester (including a 42-ester, ether (including a 42-ether), oxime, hydrazone, or hydroxylamine of rapamycin. In another embodiment, the rapamycin is 42-O-(2-hydroxy)ethyl rapamycin.

In another embodiment, the rapamycin is CCI-779, and the pack contains one or more container(s) comprising one, one to four, or more unit(s) of CCI-779.

In some embodiments, the compositions of the invention are in packs in a form ready for administration. In other embodiments, the compositions of the invention are in concentrated form in packs, optionally with the diluent required to make a final solution for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

The following examples are illustrative of the present invention, but are not a limitation thereof.

EXAMPLES

Example 1

In Vivo Testing of the Effectiveness of Treatment of Fibroids in the Eker Rat

A. Background:

The Eker rat is a well-characterized model system for uterine leiomyoma [Walker, et al., *Genes, Chromosomes, and Cancer,* 38:349-356 (2003); Houston, et al., *Cancer Research,* 63:1221-1227 (2003); and Walker, C. L., *Journal of the Society for Gynecologic Investigation,* 7(4), 249-256 (2000)]. Approximately 65% of virgin female Eker rats spontaneously develop uterine leiomyoma by 12-16 months as a result of mutation of the Tsc-2 gene.

B. Method:

Eker rats 12-16 months of age are treated with a compound useful in the invention and evaluated for tumor regression via conventional techniques and methods (e.g., ultrasound or laparascopy). RNA/protein obtained from study animals is obtained and used in vitro for characterization of the mechanism(s) of compound effectiveness.

C. Results:

A tested mTOR inhibitor, e.g., CCI-779, is expected to be effective in the treatment of uterine leiomyoma (fibroids) in the dosage range of approximately 10-250 mg/week (oral) or approximately 2-50 mg/week (intravenous). A tested rapamycin is expected to be effective at the projected oral dosage of between 0.1 mg/day to 25 mg/day.

Example 2

In Vivo Testing of the Effectiveness of Treatment of Fibroids in the Guinea Pig

A. Background:

Guinea pigs spontaneously develop fibroids as they age. This process may be accelerated by administration of estradiol, all-trans retinoic acid and troglitazone [Tsibris, et al., *J. Soc. Gynecol. Invest.,* 5(suppl1):180 (abstract)(1998); Tsibris, et al., *Cancer Res.,* 59:5737 (1999); and U.S. Pat. No. 6,218,594 B1].

B. Method:

Fibroids are induced in Guinea pigs by treatment with estradiol, all-trans retinoic acid and troglitazone. Guinea pigs are then treated with a compound useful in the invention and evaluated for tumor regression via conventional techniques and methods (e.g., ultrasound or laparascopy). RNA/protein obtained from study animals is obtained and used in vitro for characterization of the mechanism(s) of compound effectiveness.

C. Results:

A tested mTOR inhibitor, e.g., CCI-779, is expected to be effective in the treatment of uterine leiomyoma (fibroids) in the dosage range of approximately 10-250 mg/week (oral) or approximately 2-50 mg/week (intravenous). A tested rapamycin is expected to be effective at the projected oral dosage of between 0.1 mg/day to 25 mg/day.

Example 3

In Vivo Testing of the Effectiveness of Inhibition of Fibroids in the Eker Rat

A. Background:

The Eker rat is a well-characterized model system for uterine leiomyoma [Walker, et al., *Genes, Chromosomes, and Cancer,* 38:349-356 (2003); Houston, et al., *Cancer Research,* 63:1221-1227 (2003); and Walker, C. L., *Journal of the Society for Gynecologic Investigation,* 7(4), 249-256 (2000)]. Approximately 65% of virgin female Eker rats spontaneously develop uterine leiomyoma by 12-16 months as a result of mutation of the Tsc-2 gene.

B. Method:

Eker rats at approximately 9 months of age are treated with a compound useful in the invention and evaluated for tumor inhibition by comparison with a vehicle-treated control group until following the time in which vehicle-treated rats have developed tumors (about 12-16 months of age). Tumor growth is monitored via conventional techniques and methods (e.g., ultrasound or laparascopy). RNA/protein obtained from study animals is obtained and used for characterization of compound effectiveness.

C. Results:

A tested mTOR inhibitor, e.g., CCI-779, is expected to be effective in the inhibition of uterine leiomyoma (fibroids) in the dosage range of approximately 10-250 mg/week (oral) or approximately 2-50 mg/week (intravenous). A tested rapamycin is expected to be effective at the projected oral dosage of between 0.1 mg/day to 25 mg/day.

Example 4

In Vivo Testing of the Effectiveness of Inhibition of Fibroids in the Guinea Pig A. Background:

Guinea pigs spontaneously develop fibroids as they age. This process may be accelerated by administration of estradiol, all-trans retinoic acid and troglitazone [Tsibris, et al., *J.*

*Soc. Gynecol. Invest.,* 5(suppl1):180 (abstract)(1998); Tsibris, et al., *Cancer Res.,* 59:5737 (1999); and U.S. Pat. No. 6,218,594 B1].

B. Method:

Healthy Guinea pigs, not having fibroids, are treated with a compound useful in the invention and evaluated for tumor regression via conventional techniques and methods (e.g., ultrasound or laparascopy). Guinea pigs are then subjected to treatment with estradiol, all-trans retinoic acid and troglitazone, and compared to Guinea pigs not pre-treated with a compound useful in the invention. RNA/protein obtained from study animals is obtained and used in vitro for characterization of the mechanism(s) involved in fibroid tumorigenesis.

C. Results:

A tested mTOR inhibitor, e.g., CCI-779, is expected to be effective in the inhibition of uterine leiomyoma (fibroids) in the dosage range of approximately 10-250 mg/week (oral) or approximately 2-50 mg/week (intravenous). A tested rapamycin is expected to be effective at the projected oral dosage of between 0.1 mg/day to 25 mg/day.

All documents identified herein are incorporated by reference. One of skill in the art will recognize that minor modifications to the conditions and techniques described in the specific embodiments described herein can be varied without departing from the present invention. Such minor modifications and variants are within the scope of the invention as defined by the following claims.

The invention claimed is:

1. A method of treating or inhibiting uterine leiomyoma in a mammal in need thereof, which comprises providing to said mammal an effective amount of a 42-ester or 42-ether of rapamycin as the sole active agent.

2. A method of treating or inhibiting uterine leiomyoma in a mammal in need thereof, which comprises providing to said mammal an effective amount of 42-O-(2-hydroxy)ethyl rapamycin as the sole active agent.

3. A method of treating or inhibiting uterine leiomyoma in a mammal in need thereof, which comprises providing to said mammal an effective amount of rapamycin 42-ester with 3-hydroxy-2-(hydroxymethyl)-2-methylpropionic acid (CCI-779) as the sole active agent.

* * * * *